United States Patent [19]

Schwartz

[11] Patent Number: 4,600,389

[45] Date of Patent: Jul. 15, 1986

[54] DENTAL RESTORATION METHOD AND COMPOSITION THEREFOR

[75] Inventor: Abraham Schwartz, Durham, N.C.

[73] Assignee: Magnetic Activated Particle Sorting, Inc., Carrboro, N.C.

[21] Appl. No.: 665,709

[22] Filed: Oct. 29, 1984

[51] Int. Cl.⁴ .............................................. A61K 6/08
[52] U.S. Cl. .................................. 433/217.1; 106/35; 433/228.1; 523/115; 523/116; 523/118
[58] Field of Search ................................. 523/115–118; 106/35; 433/199, 217, 219, 228, 226

[56] References Cited

U.S. PATENT DOCUMENTS

| | | | |
|---|---|---|---|
| 3,309,274 | 3/1967 | Brilliant | 106/35 |
| 4,259,313 | 3/1981 | Frank et al. | 424/8 |
| 4,283,382 | 8/1981 | Frank et al. | 424/8 |
| 4,337,186 | 6/1982 | Crisp et al. | 523/116 |

*Primary Examiner*—Lorenzo B. Hayes
*Attorney, Agent, or Firm*—B. B. Olive

[57] ABSTRACT

Dental work such as in fillings, restorations, crowns and tooth glazing is assisted by use of a flourescent compound as the dental composition. The compound is made up of a rare earth chelated flourescent compound incorporated in microbeads which in turn are incorporated in a conventional composition. Observation of the site under ultraviolet radiation enables precise location of the site boundaries as excess material is removed or as the site is observed for wear after a period of time.

13 Claims, 8 Drawing Figures

DENTAL RESTORATION METHOD AND COMPOSITION THEREFOR

DESCRIPTION

1. Technical Field

This invention relates to dentistry work methods and compositions. Even more specifically, the invention relates to the use of rare earth lanthanide chelate fluorescent compounds incorporated in microbeads mixed with dental compositions enabling the boundaries of filled sites, restorations, sealants and cements to be defined and wear spots in tooth sealants to be determined.

2. Background Art

The fluorescence phenomena of rare earth chelates has been studied since the work of J. Weissman in 1942 (J. Chem Phys. 10, 214 (1942) and is referred to in U.S. Pat. No. 3,225,307. Such work related to the absorption of ultraviolet light and migration of energy through non-radiative pathways to states where fluorescence occurred at a much longer wavelength than the excitation radiation. In the past years, this type of radiation has been adapted to various laser applications (as reviewed by M. J. Weber, Chapter 14, Lanthanide and Actinide Lasers, Lanthanide and Actinide Chemistry and Spectroscopy, Edelstein, N. M. (ed.) ACS Symposium Series 131 (1980)). Several composition patents, exemplified by U.S. Pat. Nos. 3,422,023 and 3,551,345, have been issued that describe the strong flourescent properties of various lanthanide chelates. However, these patents do not describe any particular applications. An early U.S. Pat. No. 3,700,410 did describe the application of specific lanthanide chelate compounds not as fluorescent reagents but for use as optically active NMR shift reagents. Three later U.S. Pat. Nos. 4,259,313, 4,283,382 and 4,374,120 are based on fluorescent lathanide chelate compounds applied to immunological reagents. With respect to dental applications, the oxides of lanthanides, which are not considered chelates, have been added to dental porcelain to mimic the natural fluorescence of teeth under normal light as described in U.S. Pat. No. 4,198,244.

It has been known to use dental compositions for restorative materials, cements, sealants and glazes wherein the color of the material resembles the color of the teeth to which the material has been applied. Resin systems, clear and tinted sealants, and resinous dental materials available in a range of colors for matching have been used. For example, where cement is used to lute a crown to a tooth, it is desirable that the cement have the color of the tooth to which the crown is applied. Also, where a sealant is applied to seal developmental grooves or fissures, particularly for young people, or a glaze is applied to cover rough areas of fillings, the material is conventionally made to resemble in color the color of the patient's teeth or transparent to permit the tooth to be seen through it. The chemistry and application of restorative, cement and sealant materials are extensively described in the book "Restorative Dental Materials" edited by Robert G. Craig, Sixth Edition, 1980, published by The C. V. Mosby Company. Chapter 15 of this book deals with direct aesthetic restorative materials to which the invention specifically relates. In some of the described examples, ultraviolet light has been used to activate the polymerization of the materials.

Of more specific interest to the present invention, compounds have been produced as described in U.S. Pat. No. 4,198,244 that fluoresce like the teeth when exposed to an appropriate light souce. However, the fact that such known fluorescent compounds fluoresce in the same manner as the teeth makes them unsuitable for determining the boundaries of a filling or for the detection of excess sub-gingeval cement which could cause tissue irritation in the use of cements for securing crowns. Also, as another example, such prior art fluorescent materials used in dentistry in which the teeth and the compound fluoresce alike do not enable the dentist, the orthodontist, or other dental professional to determine areas from which sealants have been lost or worn.

Taking all of these considerations into mind, it would thus be desirable to have a dental work method and dental composition for restorations, fillings, cements and sealants, based on using a fluorescent material which in a specialized lighting would fluoresce in a manner different from the teeth so as to enable the boundaries of fillings and restorations and the join lines of crowns as well as wear spots in sealants to be easily located. It would be desirable, for example, for the dentist in the case of a filling to know precisely where to grind and polish a tooth in order to limit the material to the intended location and such that no excess filling material is left on the tooth surface. Also, it would be desirable in the case of a restoration to be able to remove all of the excess material used in the restoration as well as excess cement material employed with a crown. Additionally, it would be desirable in the case of sealants and glazes to be able to determine by inspection under fluorescing conditions those portions of the sealant or glaze which have been lost or worn away. The accomplishment of these various objectives thus becomes the object of the present invention. Other objects will become apparent as the description proceeds.

DICLOSURE OF INVENTION

The present invention is based on using microbead encapsulated rare earth chelated fluorescent compounds which excite in the near-ultraviolet range and intensely emit in the visible range of the spectrum, i.e., 500–700 nm, such that they may be used as components in filling materials, cements, sealants, and glazes to enable the dental professional to locate boundaries and margins during placement and finishing and also to locate areas of wear. The more useful rare earth chelate compounds for purposes of the invention are comprised of those derived from the lanthanides europium and terbium because their complexes have red and green fluorescent characteristics, respectively. These colors are a good contrast to the bluish fluorescence of teeth when exposed to the near-ultraviolet. The best chelate complex agents for this use are the water insoluble aromatic conjugated molecules which act as energy pumps to the chelated complexed rare earth ions in the $+3$ valence. These chelate complex energy pumps are found to greatly increase the fluorescence of the compounds, especially in the dry solid state. The larger aromatic highly fluorescent diketone chelators, such as napthyl acetylacetone, benzoylacetone, or benzoyltrifluoroacetone complexed with europium or terbium provide the desired insolubility in aqueous solutions. Some of the better chelates are the napthyl fluorinated acetylacetonates. Other chelate compounds deemed useful for the invention are the dibenzoyl amine and dipyridine chelates of the lanthanides.

The description which follows is directed to describing uses of such fluorescent compounds in the field of dentistry for restorative materials, cements, sealants and glazes. The value of these materials is that they are colorless when viewed under ordinary day or room light but are highly fluorescent when exposed to near-ultraviolet radiation, i.e., 300–400 nm, but preferably at about 366 nm such as the radiation from a mercury-quartz source. Such properties thus become very useful when working with restorative, cementing, sealing and glazing materials which are designed to very closely match the original material in color, texture and hardness. More specifically, the invention is directed to use of rare earth chelated fluorescent compounds incorporated into hydrophobic polymeric microbeads.

For useful incorporation into dental restorative materials, sealants, cements, and glazes, the invention recognizes that the fluorescent lanthanide chelate complexes must have chemical and physical properties such that they are compatible with the restorative material, cement, sealant, or glaze, as well as a high degree of stability with respect to fluorescence intensity and chemical leaching. The stability aspect provided by the invention is derived from incorporation of the fluorescent complexes into polymeric hydrophobic microbeads which do not allow water to penetrate and in turn to possibly leach the complex out of the microbead. The compatibility aspect of the fluorescent complexes provided by the invention is derived from the complexes being incorporated in microbeads which are not only hydrophobic, but based on compatible chemistries as the restorative material, cement, sealant, glaze or other dental materials with which they are compounded. According to the invention, the previously-described chelates are also hydrophobic, i.e., insoluble in water, to be compatible with the microbeads and dental materials' compositions.

BEST MODE FOR CARRYING OUT THE INVENTION

Figure 1:
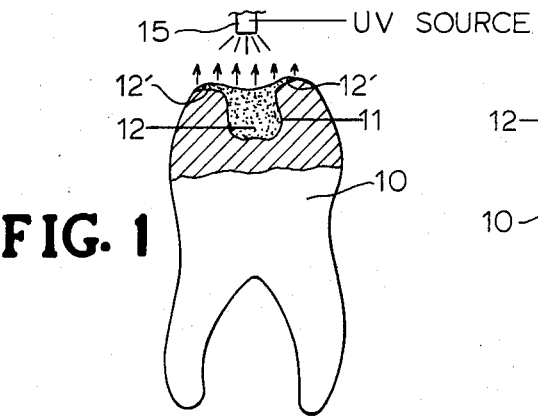
FIG. 1 is a side elevation, partially sectioned, view of a tooth having excess filling material extending over the margins of a filled cavity.

The invention can be generally described as involving the preparation of special fluorescent dental materials and using these fluorescent dental materials in restorative dental work associated, for example, with restorations, sealants, inlays, onlays and crowns. A critical feature of the invention is based on use of a rare earth chelated fluorescent compound as previously described which excites in the near-ultraviolet region and emits intensely in the visible region of the spectrum. A dental composition suited to the invention is made up by incorporating such a rare earth chelated fluorescent compound into hydrophobic polymeric microbeads. Examples of hydrophobic polymeric microbeads suited to the invention are crosslinked and non-crosslinked polyacrylates including polymethyl methacrylate and crosslinked and non-crosslinked polyaromatics including polystyrene and polyvinyltoluene. It has been observed that the typical restorative materials, cements, and sealants employed in dentistry, such as polyacrylic resins, including polymethyl methacrylate, BIS-GMA (a bisphenol A and glycidyl methacrylate conjugate) with tetraethylene glycol dimethacrylate or octafluorophenlylmethacylate, have similar hydrophobic properties. Thus, the hydrophobic polymeric microbeads containing the hydrophobic rare earth chelated fluorescent compounds of the invention have been found to be very compatible, both chemically and physically with such conventional dental compositions.

All of the mentioned encapsulating materials are known to be generally compatible with conventional restorative, cementing, glazing and sealing materials used in dentistry. Therefore, since the fluorescent materials of the invention within the microbeads are effectively isolated from the dental composition, whatever it might be, the invention is believed to have broad application to essentially any known restorative material, sealant, cement or glaze. Among the direct aesthetic restorative materials applicable to the invention are composite resins, silicate cements, glass inomer cements, zinc phosphate cements, and polyacrylic cements. Also to be observed is that since the rare earth chelated fluorescent compounds used in the invention are hydrophobic in nature, those dental compositions which are also hydrophobic in nature could be mixed directly with such rare earth chelated fluorescent compounds without incorporation in microbeads though the use of microbeads is regarded as having a significant advantage for the reasons stated.

Rare earth chelated fluorescent compounds suited to the invention include those described in U.S. Pat. No. 4,283,382 in which the fluorescent rare earth chelate comprises a fluorescent rare earth and a chelating agent selected from the group consisting of 1,3-diketones, phthalates, naphthalates; dipyridines and terpyridines; p-benzoylbenzoates, n-benzoylacetonates; and phenanthralines. Also deemed specially useful are the previously-mentioned rare earth chelate compounds derived from europium and terbium as described in U.S. Pat. No. 4,374,120 comprising fluorescent chelate of europium or terbium, a $\beta$-diketone or a dihydroxy compound, and an aminopolycarboxylic acid analogue, said chelate having a stability constant above $10^{10}$ wherein:

(a) the europium or terbium is the fluorescence emission source and is chelated to the aminopolycarboxylic acid analogue, (b) the aminopolycarboxylic acid has a functional group for covalent binding to said substance, (c) said β-diketone is selected from the group including benzoylacetone, dibenzoylmethane, thenoyltrifluoroacetone, benzoyltrifluoroacetone, 1- and 2-naphthoyltrifluoroacetone, acetylacetone, trifluoroacetylacetone, and hexafluoroacetylacetone, and other similar materials, (d) said dihydroxy compound is selected from the group including sulphosalicylic acid, the disodium salt of 3,5-pyrocatecholdisulfonic acid, 2,3-dihydroxynaphthalene, and 2,3-dihydroxynaphthalene sulfonyl acid derivatives, and other similar materials, and (e) the fluorescent 1:1:1 structure bound to the substance is formed in the presence of said β-diketone or said dihydroxy compound.

Encapsulation of the fluorescent material in microbeads has several advantages. The fluorescent material is isolated from the remainder of the dental composition. Incorporation of the lanthanide complex in the microbeads increases stability of the complex. Thus, the opportunity for leaching or dissolution of the fluorescent material is reduced. Also, by using an encapsulating material for the microbeads which is compatible with the dental composition being used, the fluorescent material confined within the microbeads is thus made compatible with the dental composition. A further advantage to be noted is that encapsulation of the fluorescent material ensures that it will not get wet therefore the fluorescent intensity will be sustained.

After the chelated fluorescent compounds have been incorporated into the polymeric microbeads, the microbeads are then incorporated into a conventional dental filling material, dental cement, dental glaze or sealant resin, depending on the particular application to which the method of the invention is being applied as later described. Since the chelates of the invention have very intense fluorescence, very little, approximately 0.001–5.0%, by weight of the chelates is required to be compounded into the restoration, filling, cement, sealant, or glazing material to allow for clear identification of boundaries, margins, or wear, as more specifically hereafter described.

Figure 2:
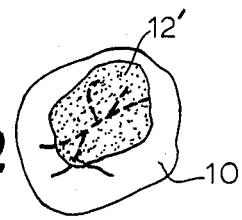
FIG. 2 is a top plan or occlusal view of the tooth of FIG. 1 with the excess filling material surrounding fissures.

Prior to describing how the invention compounds are made up, reference will be made to the drawings to illustrate the method of the invention after which the specific invention compounds will be more specifically described. Making reference initially to FIG. 1, it is assumed that a tooth 10 has a cavity 11 filled by the dental composition 12 of the invention. It is also assumed that in the initial dental work a certain amount of the invention dental composition has been also applied to the occlusal surface of the tooth around the site of the filling with such excess material 12' being indicated in FIGS. 1 and 2. It is also assumed that the dental professional desires to grind away, or otherwise remove, such excess material 12' such that the filling composition 12 of the invention is confined within the boundaries of the cavity as further illustrated in FIGS. 3 and 4. In the past, considerable guess work has been required on the part of the dental professional since the excess material over the cavity site would present the same visual appearance and thus on visual examination the dental professional could only guess at the true boundaries of the cavity.

Figure 3:
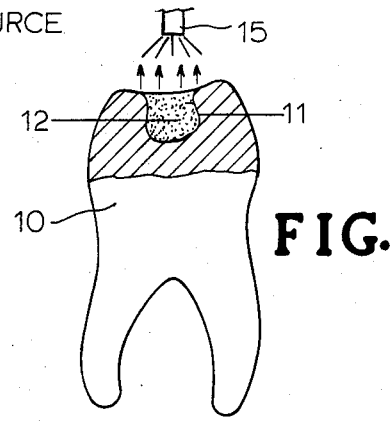
FIG. 3 is a side elevation, partially sectioned, view of the tooth of FIG. 1 with the excess filling material removed according to the invention.
Figure 4:
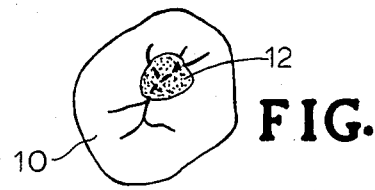
FIG. 4 is a top plan or occlusal view of the tooth of FIG. 3 with the excess filling material removed.

According to the invention after the cavity 11 has been filled with the dental composition 12 of the invention which has been hardened by polymerization, and it is known that there is excess material 12' to be removed, an ultraviolet light souce 15 is suitably directed towards tooth 10 having the excess material 12' which causes an intense emission from all of the invention composition 12, both with respect to that which is directly over the cavity 11 as well as with respect to that which is excess, namely, because the layer is thinner, the fluorescense of the excess material 12' will generally appear fuzzy or less distinct than that of the desired composition 12. While observing such fluorescence, the dental professional grinds or polishes the tooth surface while observing the fluorescence and also noting that as the excess material 12' is removed, the fuzzy fluorescent effect is also removed with respect to those areas of the tooth over which the excess material 12' resided. Once the dental professional is able to observe a sharp boundary line and uniformity of emission at which further finishing does not change, the dental professional knows that such boundary line confines the dental composition 12 of the invention and only such material. Thus, as schematically represented in FIG. 3, when all of the excess material 12' has been removed, the emissions which can be observed are emitted only from the area of the cavity 11 and nowhere else.

Figure 5:
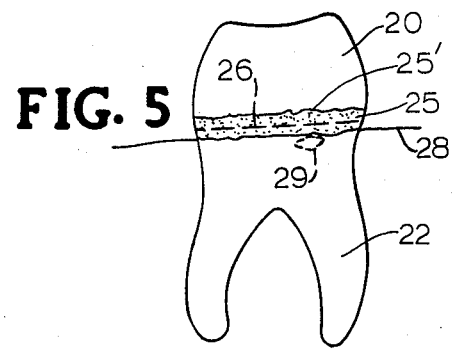
FIG. 5 is a side elevation view of a tooth having a crown cemented to the tooth, with excess cement material above and below the join line or margin, and extending into the gingival sulcus and in a dashed line circle a hypothetical deposit of extraneous cement material.

In another application illustrated in FIG. 5, it is assumed that a fluorescent dental composition 25 according to the invention has been made up, incorporated in a cement which in turn has been employed to join a crown 20 with a tooth 22 along a margin or join line 26 near the simulated gum line 28. It is also assumed in a somewhat exaggerated illustration that excess cement material 25' has been applied and it is desired to remove such excess material so as to present only the join line 26 for purposes of outward appearance and tissue health. According to the invention, after the cement has been applied as in FIG. 5, such cement is exposed to a source of ultraviolet light, as in FIG. 1, and the dental professional grinds using the fluorescence as a guide in locating excess cement to be removed, particularly any material located sub-gingivally, such as a simulated undesired cement deposit 29, or elsewhere where it can irritate soft tissue. This operation is greatly facilitated by the invention method since as the excess material 25' is ground away the dental professional will very quickly see in those areas in which all excess material 25' has been removed either no line or a single distinct barely visible sharp line 26. Also, removal of any extraneous deposit such as at 29 is facilitated.

Figure 7:
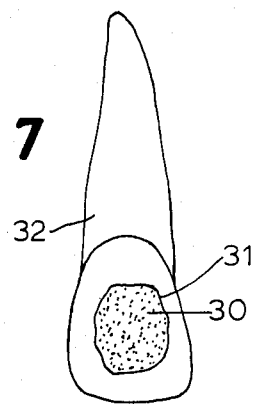
FIG. 7 is a side elevation view of an incisor tooth with a glazed area according to the invention.

As further illustrated in FIG. 7, those skilled in the art will appreciate from the foregoing description and the illustrations application of the invention to a glazing procedure. In this application, the dental operation comprises a glazing procedure to restore roughened and/or discolored tooth structure to normal texture and appearance. After the glazing composition 30 has been made up and applied to the operative site 31 on tooth 32, the glaze can be contoured while observing the extent of application under ultraviolet light thus facilitating obtaining the results desired.

Figure 8:
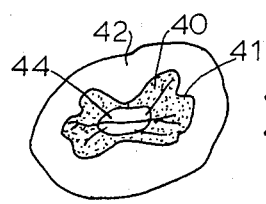
FIG. 8 is a top plan or occlusal view of a tooth with a pit and fissure sealant on portions of the occlusal surface of the tooth.

In a further example illustrated in FIG. 8, it is assumed that a sealant 40 made up according to the invention has been applied to an area 41 of a tooth 42 and it is desired to determine in due course the extent to which the sealant has been removed by normal wear or perhaps due to improper application of the sealant initially. Assuming further that after a period of time when one looks at the sealed area 41, there is in fact a spot or area 44 which is not readily visible to the eye under normal light conditions but which in fact represents an area in which the sealant compound 40 of the invention has been essentially removed by normal wear. According to the invention method, the dental professional exposes the entire face of the tooth 42 shown in FIG. 7 to an ultraviolet light source and readily observes that the spot or area 44 does not emit the intense fluorescent radiation as does the rest of the area 41. Thus, the dental professional very quickly and easily observes the precise boundaries of the worn area or spot 44 preparatory for further treatment or later observation.

Having now described the manner in which the dental composition of the invention is employed according to the invention method, an explanation will be given for making up the invention composition preparatory to use in the manner such described.

Step 1

Europium or terbium chloride is dissolved in acetone containing naphthylene trifluoroacetylacetone in molar ratio of 1:3 respectively. The resulting solution is added to water and the chelated complex is precipitated out and collected on a filter and dried. After drying, the precipitate fluoresces intensely red, in the case of europium, or green, in the case of terbium, when exposed to near-ultraviolet light at 366 nm but is white to colorless when viewed under normal day or room light.

Step 2

The compound in step 1 is incorporated into hydrophobic polymeric microbeads 0.1–5 microns, preferably 0.5 microns by either diffusion processes or incorporation during polymerization. The diffusion process is carried out by first dissolving 1.0% of the chelate compound (per weight of microbeads) in a solvent such as ethylene dichloride and then homogenizing this solution with a 0.25% sodium dodecyl sulfate aqueous solution until droplets form about 0.5 microns in size. This homogenate is then added to a stirring solution of 0.5 micron methyl methacrylate microbeads and left for 10 hours. After the microbeads are washed, examination of the resulting suspension reveals highly fluorescent red, with europium, or green, with terbium, microbeads under the fluorescent microscope when excited with near-ultraviolet radiation at 366 nm. The microbeads appear white under normal light and exhibit a hydrophobic characteristic.

Step 3

The microbeads in step 2 are, in turn, incorporated into restorative or cement materials to about 0.01–5.0%, preferably 1%, by weight for use in dental procedures. When the process is complete, the dental material is not effected either chemically or physically by the incorporation of the small amount of lanthinide chelate polymeric microbeads. Moreover, the appearance of the material is unchanged from what it would be prior to its incorporation under normal day or room lights. However, the total restoration or cement has an intense red, in the case of europium complexes, or green, in the case of terbium complexes, fluorescence under near ultraviolet light.

From the foregoing, it can be seen that by incorporating a rare earth hydrophobic chelated fluorescent compound in hydrophobic microbeads and in turn incorporating the microbeads in a conventional dental composition such as used for restorations, sealants, cements and glazes, the dental professional is provided with means for readily discerning the precise boundaries of a restoration site, the precise boundaries of a filling in a cavity, the precise join line of a crown on a tooth and precise areas of wear where a tooth has been sealed or glazed as previously described.

In practicing the invention, the area of decay or other area to be filled, restored, or the like, is prepared for receiving the invention composition. The invention microbeads are prepared beforehand and premixed with the dental composition to make up the invention filling composition. The invention composition is then applied, allowed to set, observed under ultraviolet and then ground and finished to the desired margins and boundaries.

The invention advantageously allows the dentist or other dental professional to easily and accurately determine where the restorative or cement material ends and the natural tooth begins when the material is being shaped and polished. This in turn reduces error in cutting away too much of the natural tooth or leaving excess restorative or cement material on the natural tooth which can lead to leakage of the margin and other complications. Of equal advantage is that a dental composition according to the invention is colorless under natural light, looks like the tooth itself under natural light, ordinary sunlight, or typical disco light but can be made to fluoresce intensely when illuminated with light in the 300–400 nanometer range. Thus, both the desired cosmetic appearance and ability to obtain sharp lines of demarcation between filled and non-filled areas are obtained by the invention.

Experiment 1—Filling

In one experiment, the invention microbeads were added (0.01–1.0%) to dental visible-light-cured resin that matched the color of the enamel of an extracted tooth. The tooth was drilled and prepared for filling with the microbead resin. The filling was made with the invention composition. Some of the invention composition was outside the filling as in FIGS. 1 and 2. After shaping and polishing the filling under ultraviolet light by the invention method, it appeared as a normal tooth under normal light and difficult to identify as a filling; however, under ultraviolet light, the filling and its sharp boundary, as in FIGS. 3 and 4, were bright red whereas the real tooth glowed slightly bluish.

Experiment 2—Crown

Figure 6:
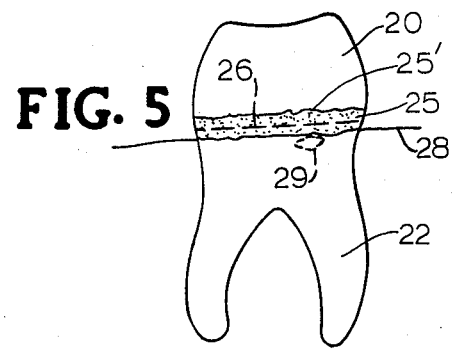
FIG. 6 is a side elevation view of the tooth and crown of FIG. 5 with the excess cement material removed at the join line or margin according to the invention.

In another experiment, microbeads were added to dental cement which was used for affixing a crown on a tooth. After shaping and polishing under ultraviolet light by the invention method the cement appeared as part of a normal tooth under regular light, but the join line appeared as a fine red line under ultraviolet light as in FIG. 6.

Other more specific examples are given below illustrating application of the invention to a wide range of dental work:

Example 1

Restoration

A tooth was prepared for restoration in the normal way with the removal of decay and cutting of retention bevels. One percent by weight of 3 micron polymethyl methacrylate microbeads containing europium chelated with naphthyl trifloroacetonate was mixed with the composite resin component of the VISIO-FIL restoration system (L. D. Caulk, Inc.). The tooth was then filled in the normal manner. After exposing the filled tooth to the proper polymerizing light source, the restoration was ground and shaped in the usual way with intermittent examination under a near-ultraviolet light source which made the restoration fluoresce an intense red while the tooth appeared as a bluish white. Such examination throughout the shaping process allowed the operator to know when the tooth surface was exposed under the excess restoration material.

Example 2

Crown Cementation

A crown was prepared for cementing onto a tooth in the usual way. To the powder component of the Fleck's Cement system (Mizzy, Inc.) was mixed one percent of the 3 micron polymethyl methacrylate microbeads containing europium chelated with napthyl trifloroacetonate. The liquid component of the system was then mixed in with the powder in the usual way and used as the cement to hold the crown on the tooth. After the cement hardened the excess cement was ground away with intermittent examination under a near-ultraviolet light source which made the cement fluoresce an intense red while the crown and tooth appeared bluish white. With such examination, the excess cement was removed with a minimal removal of the crown and tooth material. After final shaping, the cement appeared as a sharp line between the tooth and crown.

Example 3

Sealant

An auto curing sealant, Delton (Johnson & Johnson), was prepared in the usual way with the addition of one percent of 3 micron polymethyl methacrylate microbeads containing euopium chelated with napthyl trifloroacetonate added to the resin component prior to mixing with the liquid initiator. The sealant was applied to the teeth in the usual way and allowed to set. Examination under a near-ultraviolet light source revealed that the areas covered with sealant appeared red while the areas not covered with the sealant appeared bluish white. After grinding away spots on the sealant, to simulate wear, the ground spots also appeared bluish white in the field of red when exposed to the ultraviolet light source.

From the experiments and examples given, it can thus be seen that the invention advantageously allows the dentist or other dental professional to easily and accurately determine where the restorative or cement material ends and the natural tooth begins when the material is being shaped and polished. This in turn reduces error in cutting away too much of the natural tooth or leaving excess restorative or cement material on the natural tooth which can lead to leakage of the margin and other complications. Of equal advantage is that a dental composition according to the invention is colorless under natural light, looks like the tooth itself under natural light, ordinary sunlight, or typical disco light but can be made to fluoresce intensely in the 300–400 nanometer range. Thus, both the desired cosmetic appearance and ability to obtain sharp lines of demarcation between filled and non-filled areas are obtained by the invention.

What is claimed is:

1. A method for dental restorations in which a dental compound adapted to set and harden after application is applied to a selected site, comprising the steps of:

(a) making up the dental compound to be applied to the operation by incorporating microbeads containing a fluorescent rare earth chelated compound in said dental compound, said microbeads functioning to permanently isolate said fluorescent compound within said microbeads. incorporated with said dental compound wherein said dental compound is not fluorescent in the wavelengths in which said fluorescent compound fluoresces;
    (b) applying the dental compound to the site of the desired operation and allowing such compound to set and harden at the site; and
    (c) observing the site under radiation at a wavelength selected to cause said fluorescent compound to fluoresce while isolated in said microbeads as a step preparatory to said restoration.

2. A method as claimed in claim 1 wherein said dental restoration comprises filling a tooth and including the step of removing excess said dental compound from around the filling site while observing the difference in color on opposite sides of the border of the site when under said radiation.

3. A method as claimed in claim 1 wherein said dental restoration comprises cementing a crown to a tooth with a join line having excess said dental compound on one or more sides thereof and including the step of removing said excess dental compound while observing the difference in color on opposite sides of the border and adjacent areas of the site of said operation when under said radiation.

4. A method as claimed in claim 1 wherein said dental restoration comprises pit and fissure sealing and including the step of observing the tooth to which a sealant has been applied under ultraviolet radiation after a period of use of the sealed tooth to locate differences in the amount of said dental compound at the site of said sealing.

5. A method as claimed in claim 1 wherein said dental restoration comprises glazing a tooth and including the step of contouring the glaze while observing the extent of application under ultraviolet radiation.

6. A method as claimed in claim 1 wherein:
    (a) said fluorescent compound is a hydrophobic rare earth chelated ultraviolet fluorescent compound;
    (b) said microbeads comprise hydrophobic polymeric microbeads;
    (c) said dental compound is normally not fluorescent in the near-ultraviolet range; and
    (d) the radiation under which said site is observed is ultraviolet radiation.

7. A method as claimed in claim 6 wherein said rare earth chelated compound is selected from the group consisting of compounds derived from europium and terbium.

8. A method as claimed in claim 6 wherein said dental compound is selected from the group consisting of composite resins, silicate cements, zinc phosphate cements and polyacrylic cements.

9. A method as claimed in claim 7 in which the chelate of said rare earth chelated compound is selected from the group consisting of 1,3-diketones, phthalates, naphthalates; dipyridines and terpyridines.

10. A dental composition useful under ultraviolet light exposure for exhibiting its boundaries and margins after being applied in restorations comprising:
    (a) polymeric hydrophobic microbeads containing a rare earth chelated compound characterized by being hydrophobic and fluorescent in the visible range under ultraviolet illumination, said microbeads functioning to permanently isolate said fluorescent compound therein; and (b) a hardenable dental restorative material.

11. A dental composition as claimed in claim 10 wherein:

(a) said rare earth chelated compound is selected from the group consisting of compounds derived from europium and terbium and in which the chelate of said rare earth chelated compound is selected from the group consisting of 1,3-diketones, phthalates, naphthalates; dipyridines and terpyridines;

(b) said dental compound is selected from the group consisting of composite resins, silicate cements, zinc phosphate cements and polyacrylic cements;

(c) said polymeric hydrophobic microbeads are formed from a polymer selected from the group consisting of polymethyl methacrylate polystyrene and polyvinyltolulene.

12. A method as claimed in claim 1 wherein said dental compound, fluorescent compound and microbeads are each of hydrophobic character.

13. A dental composition as claimed in claim 10 wherein said rare earth compound, microbeads and dental composition are each of hydrophobic character.

* * * * *